(12) United States Patent
Maeno et al.

(10) Patent No.: US 7,279,081 B2
(45) Date of Patent: Oct. 9, 2007

(54) ELECTROCHEMICAL SENSOR

(75) Inventors: Tatsuo Maeno, Tokyo (JP); Hiromi Nakano, Tokyo (JP)

(73) Assignee: Nemoto & Co., Ltd., Tokyo (JP)

( * ) Notice: Subject to any disclaimer, the term of this patent is extended or adjusted under 35 U.S.C. 154(b) by 857 days.

(21) Appl. No.: 10/674,037

(22) Filed: Sep. 29, 2003

(65) Prior Publication Data

US 2004/0079637 A1 Apr. 29, 2004

(30) Foreign Application Priority Data

Sep. 27, 2002 (JP) ............................. 2002-284433
Sep. 27, 2002 (JP) ............................. 2002-284434

(51) Int. Cl.
*G01N 27/403* (2006.01)
(52) U.S. Cl. ..................... 204/432; 204/431
(58) Field of Classification Search ............... 204/431, 204/432
See application file for complete search history.

(56) References Cited

FOREIGN PATENT DOCUMENTS

| GB | 8103258 | | 2/1981 |
|---|---|---|---|
| GB | 2235050 A | * | 2/1991 |
| JP | 57-147048 | | 10/1982 |
| JP | 06-058906 | | 3/1994 |
| JP | 06-300735 | | 10/1994 |
| JP | 06-242059 | | 9/1996 |
| WO | WO 99/24826 A1 | * | 5/1999 |

OTHER PUBLICATIONS

Kirk-Othmer Encyclopedia of Chemical technology, fourth edition, vol. 9, pp. 90-95, 1994.*

* cited by examiner

*Primary Examiner*—Alex Noguerola
(74) *Attorney, Agent, or Firm*—Dennis G. LaPointe (57) ABSTRACT

Electrolytic solution which contains sulfuric acid and is stored in an electrolytic solution storage 2 of a case 3 is caused to be retained in an electrolytic solution retainer 25. A reference electrode 18 and a counter electrode 19 are printed on the underside of the electrolytic solution retainer 25. The reference electrode 18, the counter electrode 19, and the electrolytic solution retainer 25 are thus formed into a single component, with the reference electrode 18 and the counter electrode 19 being formed simultaneously. Electrode pins 32,33,34 are brought into contact with the reference electrode 18, the counter electrode 19, and a detection electrode 17. The electrode pins 32,33,34 are made of tantalum. A contact portion 32b,33b,34b and a lead portion 32a,33a,34a of each electrode pin 32,33,34 are formed as a seamless, integral body.

15 Claims, 5 Drawing Sheets

ELECTROCHEMICAL SENSOR

TECHNICAL FIELD

The present invention relates to an electrochemical sensor having a detection electrode, a reference electrode, and a counter electrode.

BACKGROUND OF THE INVENTION

A conventional electrochemical gas sensor, which is an electrochemical sensor of this type, is designed with such factors as retention of electrolytic solution and permeation of the electrolytic solution to the electrodes being taken into consideration. Therefore, it requires many parts and is difficult to be made compact.

Figure 6:
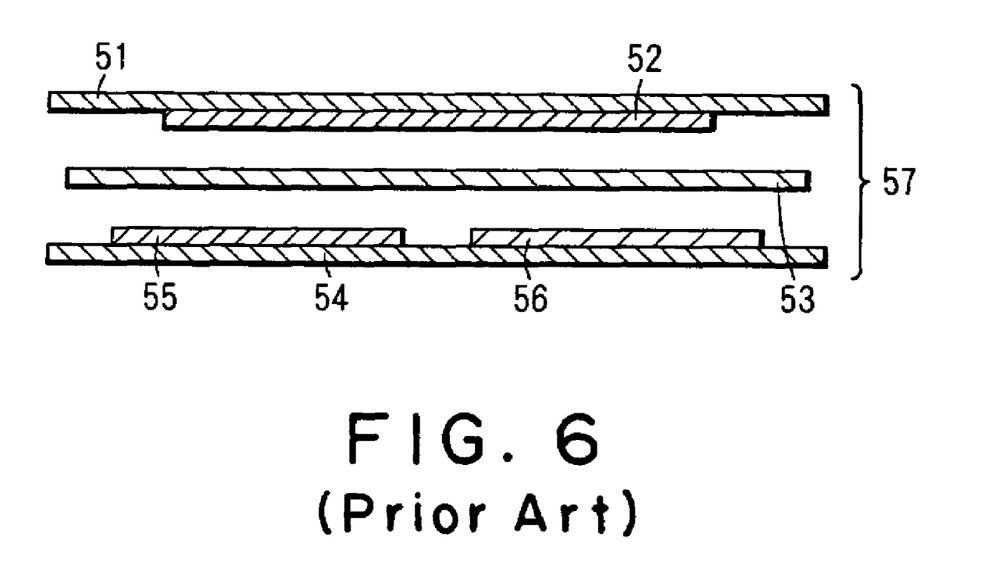
FIG. 6 is a cell of a sectional view of a conventional electrochemical sensor.

An example of electrochemical gas sensors of this type is shown in FIG. 6. The electrochemical gas sensor shown in FIG. 6 includes a porous base member 51, which made of fluorine-contained resin or the like and is hydrophobic as well as gas permeable. A detection electrode 52 is formed on the base member 51 by printing or other process. Facing the base member 51 is an electrolytic solution retainer 53 which servers to retain electrolytic solution and cause the electrolytic solution to permeate into the electrodes 52,55,56. A porous member 54 is provided to serve as another base member which is hydrophobic as well as gas permeable. The reference electrode 55 and the counter electrode 56 are provided on the porous member 54 and disposed in contact with the electrolytic solution retainer 53. The detection electrode 52, the reference electrode 55, the counter electrode 56, and the electrolytic solution retainer 53 together form a cell 57.

Japanese Patent Provisional Publication No. 1982-147048 discloses a structure wherein electrolytic solution is caused to permeate into electrodes by feeding the electrolytic solution into an electrolytic solution retainer in a cell portion. The cell portion is contained in a case and located towards one end of the case. A hydrophilic liquid guiding member continuously feeds the electrolytic solution from an electrolytic solution storage, which is located towards the other end of interior of the case, into the electrolytic solution retainer in the cell.

Another conventionally known structure is disclosed in Japanese Patent Provisional Publication No. 1994-58906, which calls for causing electrolytic solution to permeate into an electrolytic solution retainer in a cell by bringing the electrolytic solution retainer into direct contact with the electrolytic solution or by using a tubular liquid guiding member. Yet another conventionally known structure is disclosed in Japanese Patent Provisional Publication No. 1994-242059, which calls for causing electrolytic solution to permeate by using a slight gap between the inner wall of an electrolytic solution storage and a ring, which is a separate body from the inner wall of the electrolytic solution storage.

Aqueous solution of sulfuric acid is normally used as the electrolytic solution. However, as sulfuric acid solution is hygroscopic, the sulfuric acid solution used as the electrolytic solution absorbs moisture in the atmosphere and thereby gradually increases the quantity of the electrolytic solution in the electrolytic solution storage of the case. As a result, the pressure in the electrolytic solution storage increases due to the sulfuric acid solution that has absorbed moisture. The increased pressure in the electrolytic solution storage presents the possibility of leakage of the sulfuric acid solution from the electrolytic solution storage.

An example of means to release the pressure to the outside in order to prevent leakage of the sulfuric acid solution from the electrolytic solution storage is disclosed in Japanese Patent Provisional Publication No. 1982-147048 mentioned above, which calls for providing the bottom of the electrolytic solution storage with a gas drain hole that serves as an air vent and closing off the gas drain hole with a porous filter that is hydrophobic as well as gas permeable. The aforementioned Japanese Patent Provisional Publication No. 1994-58906 describes another example, which calls for providing an absorbent inside the electrolytic solution storage to absorb and retain electrolytic solution, thereby absorbing the increased electrolytic solution and, consequently, absorbing fluctuation in the pressure. The aforementioned Japanese Patent Provisional Publication No. 1994-242059 describes yet another example, which calls for permitting air to enter or exit by means of providing porous polytetrafluoroethylene (PTFE) rods or the like inside the electrolytic solution storage.

As described in, for example, Japanese Patent Provisional Publication No. 1994-300735, an electrochemical gas sensor, which is an electrochemical sensor of the type described above, is typically provided with a case that includes an electrolytic solution storage to store electrolytic solution therein. A detection electrode, a reference electrode, and a counter electrode are disposed in the case. Electrode pins are attached to the case. The electrode pins are a plurality of conductors that pass through the case so as to extend from the detection electrode, the reference electrode, and the counter electrode to the outside.

In order to draw outputs from the detection electrode, the reference electrode, and the counter electrode to the outside, each electrode pin is in contact with each respective one of these electrodes. Each electrode pin has a lead portion formed of a metal selected from the group of metals consisting of titanium (Ti), tantalum (Ta), zirconium (Zr), or alloy that contains at least one of these metals. A ribbon portion which has a narrow strip-like shape and made of platinum (Pt) is welded to the distal end of each lead portion. Each ribbon portion is adapted to come into contact and become electrically connected with each respective one of the electrodes, i.e. the detection electrode, the reference electrode, or the counter electrode.

It is also a known practice to form the lead portions of the electrodes of an alloy containing copper (Cu), Nickel (Ni) or titanium.

In cases where the electrolytic solution is drawn up by the hydrophilic liquid guiding member in the case, the liquid guiding member has to be disposed so as to penetrate into the cell. Should there be a plurality of layers of electrolytic solution retainers inside the cell in a structure that calls for the electrolytic solution retainer(s) to have the ability to come into contact with the electrolytic solution, the layers of the electrolytic solution retainers have to be arranged so that the electrolytic solution is sufficiently fed to all the electrolytic solution retainers. Therefore, either structure requires a large number of parts and a complicated production process and is difficult to be made compact.

The structure that calls for using platinum (Pt) to form the ribbon portions welded to the distal ends of the lead portions of the electrode pins of the electrochemical sensor presents the problem of increased production costs, because though platinum is highly anti-corrosive, it is very expensive. Forming the lead portions of the electrode pins of copper or a copper alloy results in superior external pins which are drawn out of the case. Due to poor anti-corrosion properties, however, it is not easy to ensure sufficient durability of such electrodes.

Forming each electrode of two parts, i.e. a lead portion and a ribbon portion, increases the number of parts and the number of welding steps, resulting in increased production costs. Furthermore, there arises the possibility of contact failure resulting from improper welding or electric corrosion at the portion where the lead portion and the ribbon portion are welded to each other, or insufficient mechanical strength, etc. Forming each electrode of a lead portion and a ribbon portion presents such other problems as formation of a local cell, which would impair the measurement precision, and a complicated structure of the electrode pins, which would make it difficult to ensure sufficient reliability.

In order to solve the above problems, an object of the invention is to provide an electrochemical sensor which is easy to produce and make compact.

DISCLOSURE OF THE INVENTION

An electrochemical sensor according to the invention includes a base member which has a porous, sheet-like shape and is hydrophobic as well as gas permeable, a detection electrode which is included in the base member and contains a catalyst and hydrophobic resin, a reference electrode which contains a catalyst and hydrophobic resin, a counter electrode which contains a catalyst and hydrophobic resin, and an electrolytic solution retainer which has a sheet-like shape and is hydrophilic as well as electrically insulating, wherein the electrolytic solution retainer is provided with either one of or both the reference electrode and the counter electrode.

As described above, the base member is provided with the detection electrode, while the electrolytic solution retainer is provided with at least one of the other electrodes, i.e. the reference electrode or the counter electrode. By thus integrating the electrolytic solution retainer with either one of or both the reference electrode and the counter electrode in a single component, the configuration described above reduces the number of parts and facilitates production of the electrochemical sensor as well as reduction of its size.

According to another feature of the invention, the reference electrode and the counter electrode are formed on one of the planar surfaces of the electrolytic solution retainer.

As the reference electrode and the counter electrode are formed on one of the planar surfaces of the electrolytic solution retainer, the electrolytic solution retainer, the reference electrode, and the counter electrode are integrated in a single component. As this configuration enables not only the further reduction of the number of parts but also the simultaneous formation of the reference electrode and the counter electrode on the electrolytic solution retainer, this configuration further facilitates production of the electrochemical sensor as well as reduction of its size.

According to yet another feature of the invention, the reference electrode is formed on one of the planar surfaces of the electrolytic solution retainer, and the counter electrode is formed on the other planar surface of the electrolytic solution retainer.

As the reference electrode and the counter electrode are respectively formed on the two planar surfaces of the electrolytic solution retainer, the electrolytic solution retainer, the reference electrode, and the counter electrode are integrated in a single component. By thus enabling the further reduction of the number of parts, this configuration further facilitates production of the electrochemical sensor as well as reduction of its size.

According to yet another feature of the invention, the reference electrode and the counter electrode are formed of the same material on the electrolytic solution retainer.

Using the same material to form the reference electrode and the counter electrode on the electrolytic solution retainer further facilitates the formation of the reference electrode and the counter electrode on the electrolytic solution retainer.

An electrochemical sensor according to yet another feature of the invention includes a case having an electrolytic solution storage, a cap adapted to be fitted to the case, a cell adapted to be contained in the case by means of said cap, and electrode pins which are included in either one of or both the case and the cap and adapted to be connected to said cell, said cell including a base member which has a porous, sheet-like shape and is hydrophobic as well as gas permeable, a detection electrode which is included in the base member and contains a catalyst and hydrophobic resin, a reference electrode which contains a catalyst and hydrophobic resin, a counter electrode which contains a catalyst and hydrophobic resin, and an electrolytic solution retainer which has a sheet-like shape and is hydrophilic as well as electrically insulating, wherein the electrolytic solution retainer is provided with either one of or both the reference electrode and the counter electrode.

As described above, the detection electrode is included in the base member of the cell which is adapted to be contained in the case having the electrolytic solution storage by means of said cap, and the electrolytic solution retainer of the cell is provided with either one of or both the reference electrode and the counter electrode. By thus integrating the electrolytic solution retainer with either one of or both the reference electrode and the counter electrode in a single component, the configuration described above reduces the number of parts and facilitates production of the electrochemical sensor as well as reduction of its size.

An electrochemical sensor according to yet another feature of the invention further includes at least one post element that is located inside the electrolytic solution storage of the case and provided with one or more grooves adapted to guide the electrolytic solution contained in the electrolytic solution storage to the electrolytic solution retainer of the cell.

As the electrolytic solution retainer of the case is provided with a post element in which one or more groove for guiding the electrolytic solution from the electrolytic solution storage to the electrolytic solution retainer of the cell is formed, there is no need of attaching another member or element to the interior of the electrolytic solution storage of the case. Therefore, the number of parts to form the electrochemical sensor is not increased. Furthermore, as this structure permits the electrolytic solution in the electrolytic solution storage to be guided and permeated into the electrolytic solution retainer of the cell by means of capillary action via the groove portion(s) of the post element, this configuration enables the further reduction of the number of parts and further facilitates production of the electrochemical sensor as well as reduction of its size.

The electrolytic solution storage of the case of an electrochemical sensor according to yet another feature of the invention is provided with a plurality of post elements adapted to support the cell, which is contained in the electrolytic solution storage of the case, wherein one or more of said post elements are provided with grooves adapted to guide the electrolytic solution contained in the electrolytic solution storage to the electrolytic solution retainer of the cell. With the configuration described above, the cell contained in the electrolytic solution storage of the case are supported by a plurality of post elements. Therefore, with these post elements functioning as supports, the configuration described above makes it possible to support the electrolytic solution retainer and the base member between the case and the cap by means of the post elements without the possibility of deformation of the electrolytic solution retainer or the base member. Furthermore, the post elements also hold the electrolytic solution retainer in close contact with the detection electrode.

The electrolytic solution retainer of an electrochemical sensor according to yet another feature of the invention is formed of glass wool.

Using glass wool to form the electrolytic solution retainer facilitates production of the electrolytic solution retainer and also makes it possible to form either one of or both the reference electrode and the counter electrode on the electrolytic solution retainer by printing or any other appropriate process. Therefore, this feature further facilitates production of the reference electrode and the counter electrode on the electrolytic solution retainer.

An electrochemical sensor according to yet another feature of the invention further includes a porous sheet which is hydrophobic as well as gas permeable and contained in said case in such a state as to be in contact with the electrolytic solution storage of the case and the base member positioned in the case.

The configuration described above, which calls for disposing a porous sheet that is hydrophobic as well as gas permeable inside the case in such a state as to be in contact with the electrolytic solution storage of the case and the base member in the case, makes it possible, without providing the case or the cap with any other opening or the like, to release gas in the electrolytic solution storage to the outside, thereby preventing leakage of the electrolytic solution from the case. Therefore, leakage of the electrolytic solution can be prevented easily in a simple configuration.

An electrochemical sensor according to yet another feature of the invention includes a case having an electrolytic solution storage adapted to store therein electrolytic solution containing sulfuric acid, a cap adapted to be fitted to the case, electrodes consisting of a detection electrode, a reference electrode, and a counter electrode, each of which is adapted to be contained in either the case or the cap, and electrode pins each of which has a contact portion and a lead portion that is drawn out of either the case or the cap, said contact portion of each electrode pin is adapted to secure each respective one of said electrodes, i.e. the detection electrode, the reference electrode, or the counter electrode, in the case or the cap in such a state as to be in contact with the electrode, wherein the contact portion and the lead portion of each electrode pin is formed as a seamless, integral body of either tantalum or an alloy containing tantalum.

Tantalum is not only resistant to corrosion from sulfuric acid but also relatively inexpensive. Therefore, in cases where the electrolytic solution in the electrolytic solution storage of the case contains sulfuric acid, the electrode pins are formed of tantalum or a tantalum alloy, with the contact portion and the lead portion of each electrode pin formed as a seamless, integral body, wherein each lead portion is adapted to come into contact with each respective one of said electrodes contained in the case or the cap to be fitted to the case, in other words the detection electrode, the reference electrode, or the counter electrode, and each lead portion is drawn out of either the case or the cap. This configuration not only ensures that the electrode pins have sufficient resistance to corrosion from sulfuric acid but also improves manufacturability of the electrode pins. As tantalum has relatively high degree of rigidity, the rigidity of each electrode pin formed of tantalum or a tantalum alloy as a seamless, integral body ensures that at least one of the electrodes comprised of the detection electrode, the reference electrode, and the counter electrode is supported inside the case and that the electrode pins reliably come into contact with the detection electrode, the reference electrode, and the counter electrode, respectively.

The electrode pins of an electrochemical sensor according to yet another feature of the invention are formed integrally with either one of the case or the cap.

As the electrode pins are formed as an integral body with the case or the cap, the electrode pins and either one of the case or the cap are formed as a single component. By thus simplifying the structure and reducing the number of parts, this configuration reduces the number of processing steps required to assemble the electrochemical sensor and improves the manufacturability of the electrochemical sensor further.

Each electrode pin of an electrochemical sensor according to yet another feature of the invention has at least one bent portion to immovably hold each respective one of the detection electrode, the reference electrode, or the counter electrode in either the case or the cap.

According to the configuration described above, each one of the detection electrode, the reference electrode, or the counter electrode is immovably held in either the case or the cap by means of the bent portion(s) of each respective electrode pin. As a result, the spring function of the bent portion(s) of each electrode pin reliably immovably holds each respective one of the detection electrode, the reference electrode, or the counter electrode in the case or the cap and, simultaneously, ensures reliable contact of the electrode pin with each respective one of the detection electrode, the reference electrode, or the counter electrode.

The electrode pins of an electrochemical sensor according to yet another feature of the invention are formed integrally with the case by molding.

As the electrode pins are formed as an integral body with the case by molding, the electrode pins and the case are formed as a single component. By thus simplifying the structure of the electrode pins and the case and reducing the number of parts required to produce them, this configuration reduces the number of processing steps required to assemble the electrochemical sensor and improves the manufacturability of the electrochemical sensor further.

PREFERRED EMBODIMENT OF THE INVENTION

Next, an electrochemical sensor according to an embodiment of the present invention is explained hereunder, referring to FIGS. 1 through 5.

Referring to FIGS. 1 through 5, numeral 1 denotes an electrochemical gas sensor serving as an electrochemical sensor. The electrochemical gas sensor 1 includes a case 3 in the shape of a substantially rectangular box with a bottom. An electrolytic solution storage 2 having a substantially recess-shaped cross section is formed inside the case 3. The case 3 is formed of an acid resisting resin, such as polyphenylene oxide (PPO) or polyphenylene ether (PPE).

A cap 4 in the shape of a substantially rectangular box with a base is snugly fitted to the case 3 so as to close off the electrolytic solution storage 2 in a watertight state. The cap 4 is formed of the same material as the case 3. In the explanation hereunder, the portion of the electrochemical gas sensor 1 where the case 3 is located is referred to as the bottom portion 5, and the upper portion means the portion of the electrochemical gas sensor 1 where the cap 4 is provided.

The bottom portion of the case 3 includes a base face 11, which is a flat surface. An outer wall portion 12 which has a shape of a substantially rectangular tube and projects upward is integrally formed on the base face 11. The outer wall portion 12 extends along the perimeter of the base face 11 at a slight distance from the edge of the base face 11. The space defined by the inner surface of the outer wall portion 12 and the upper surface of the base face 11 serves as the aforementioned electrolytic solution storage 2. A given quantity of electrolytic solution 13 is injected into the electrolytic solution storage 2 and stored therein. The electrolytic solution 13 is comprised of sulfuric acid solution, which is an aqueous solution containing sulfuric acid ($H_2SO_4$).

A plurality of inner ribs 14 (for example, 6 inner ribs 14) are provided inside the outer wall portion 12 of the case 3. The inner ribs 14 have a flat, strip-like shape and extend vertically along the outer wall portion 12. In the case of the present embodiment, two each inner ribs 14 that are spaced apart are provided at each lateral side and one of the two lengthwise ends of the outer wall portion 12 as viewed in FIG. 1. The inner ribs 14 are formed as an integral, continuous body with the base face 11 of the case 3. Each inner rib 14 is formed so that its upper end is located lower than the upper end of the outer wall portion 12 and extends parallel to the base face 11 of the case 3.

A plurality of vertical protrusions 15 (for example, 7 vertical protrusions 15) serving as post elements are formed inside the case 3 as an integral body with the base face 11. The vertical protrusions 15 are located near the center of the base face 11 and project upward from the base face 11. As shown in FIGS. 1 through 4, three vertical protrusions 15 are arranged near the center of the base face 11 in such a manner as to be spaced apart in the lengthwise direction of the base face 11 and extend parallel to one another. The other four vertical protrusions 15 are spaced apart and extend parallel to one another so as to nearly close off the spaces between the aforementioned three vertical protrusions 15.

Feeding grooves 16 having a wave-shaped cross section are formed on both sides of each one of the vertical protrusions 15 that are not located at the center. The feeding grooves 16 extend vertically with respect to the case 3, in other words in the heightwise direction of the vertical protrusions 15. Each feeding groove 16 is formed so as to extend from the base face 11 of the case 3 to the distal end, i.e. the upper end, of the corresponding vertical protrusion 15. The feeding grooves 16 serve to guide the electrolytic solution 13, which is stored in the electrolytic solution storage 2 of the case 3, to the upper portions of the vertical protrusions 15 by means of capillary action.

Each vertical protrusion 15 has three feeding grooves 16: one at the widthwise center of one side of the vertical protrusion 15, and two at the other side of the vertical protrusion 15. The two feeding grooves 16 are arranged such that one each is located towards each respective widthwise end of the other side of the vertical protrusion 15, at a given distance from the corresponding end.

Provided in the space that is formed between the vertical protrusions 15 in the case 3 and the cap 4 when the cap 4 is fitted to the case 3 is a cell 21, which has a detection electrode 17, a reference electrode 18, and a counter electrode 19. The detection electrode 17 contains a catalyst and hydrophobic resin. The catalyst of the detection electrode 17 is made of a material that contains at least one element selected from the group consisting of platinum (Pt), gold (Au), and palladium (Pd).

The hydrophobic resin consists of low-molecular fluorine-contained resin and high-molecular fluorine-contained resin which are mixed at an appropriate mixing ratio. In the case of the present embodiment, low-molecular polytetrafluoroethylene and high-molecular polytetrafluoroethylene are used as the low-molecular fluorine-contained resin and the high-molecular fluorine-contained resin, respectively. The high-molecular polytetrafluoroethylene is used in a dispersed state, by dispersing fine grains of high-molecular polytetrafluoroethylene in water or an organic solvent.

By printing or any other appropriate means, the detection electrode 17 of the cell 21 is formed directly on one of the two planar surfaces of a base member 22, which has a sheet-like shape and also serves as a sealing member. The base member 22 is made of fluorine-contained resin, such as polytetrafluoroethylene (PTFE). The base member 22 is formed in the shape of a substantially rectangular porous sheet having a length and a width that are greater than the length and the width of the base face 11 of the case 3, respectively. The porous base member 22 is hydrophobic as well as gas permeable; it does not let liquid through while being permeable to gas.

In the explanation hereunder, the planar surface of the base member 22 on which the detection electrode 17 is printed as described above may be referred to as the main surface of the base member 22. One of the functions of the base member 22 is to permit watertight fitting between the cap 4 to the case 3. The base member 22 is designed to be placed on the top of the outer wall portion 12 of the case 3, with the main surface of the base member 22, which faces towards the bottom portion 5, facing the base face 11 of the case 3. When the cap 4 is fitted over the outer wall portion 12 of the case 3 in this state, the rim of the base member 22 is sandwiched between the case 3 and the cap 4, thereby sealing the gap between the case 3 and the cap 4 in a watertight state.

Figure 1:
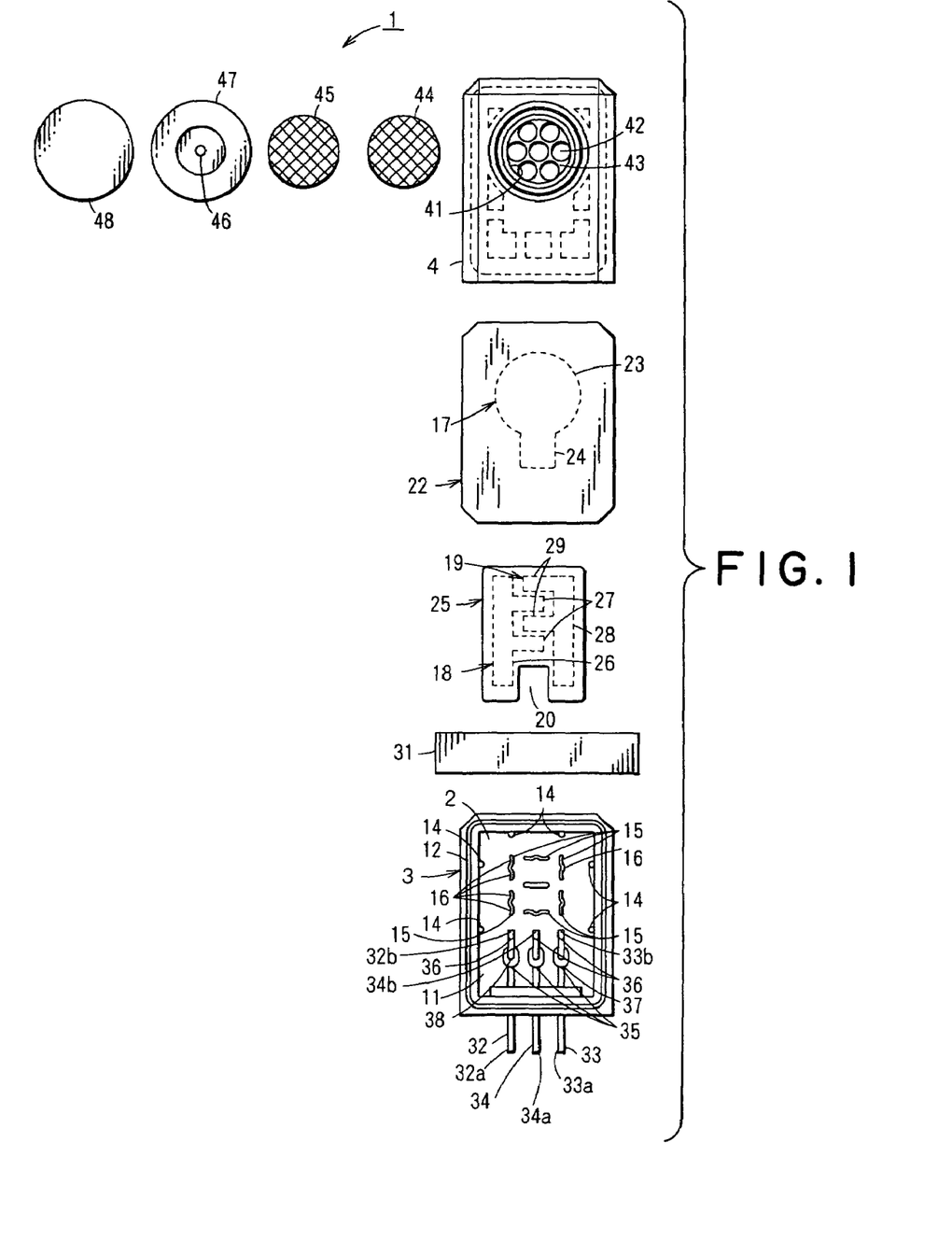
FIG. 1 is an exploded top view of an electrochemical sensor according to an embodiment of the present invention.

As shown in FIG. 1, the detection electrode 17 printed on the main surface of the base member 22 has a circular detection surface 23, which is provided at the approximate middle of the width of the main surface of the base member 22. The detection surface 23 is located between one of the lengthwise ends and the middle of the length of the main surface of the base member 22. A narrow, rectangular contact tab 24 is formed integrally with the detection surface 23 and extends along the normal of the detection surface 23, towards the other lengthwise end of the main surface of the base member 22. To be more specific, the contact tab 24 projects from a part of the rim of the detection surface 23 in the lengthwise direction of the main surface of the base member 22.

Each one of the other electrodes of the cell 21 mentioned above, i.e. the reference electrode 18 and the counter electrode 19, contains the same catalyst and hydrophobic resin as those of the detection electrode 17 of the cell 21. The reference electrode 18 and the counter electrode 19 are formed on the same planar surface, i.e. the underside, of an electrolytic solution retainer 25, which is in the shape of a sheet. By thick-film printing, such as screen printing, or any other appropriate means, the reference electrode 18 and the counter electrode 19 are formed of the same material in a comb-like shape directly on the electrolytic solution retainer 25 in the same production process. The interior of the electrolytic solution retainer 25 is permeated with the catalyst to some extent, for example, to approximately one-third of the thickness of the electrolytic solution retainer 25, thereby ensuring close contact of the reference electrode 18 and the counter electrode 19 with the electrolytic solution retainer 25. Therefore, an electrode layer that is highly resistant to vibration and impact is formed.

The electrolytic solution retainer 25 is formed in a sheet-like shape of glass fiber, such as glass wool, or any other appropriate material that is hydrophilic as well as electrically insulating. A cutout recess 20 is formed by cutting out the middle portion one of the lengthwise ends of the electrolytic solution retainer 25. The electrolytic solution retainer 25 is disposed on the upper ends of the vertical protrusions 15 of the case 3 and thus supported on the vertical protrusions 15 in the state where the reference electrode 18 and the counter electrode 19 printed on the same planar surface face downward. When contained in the case 3, the electrolytic solution retainer 25 is placed on the inside of the inner ribs 14 of the case 3.

As shown in FIGS. 1 through 4, the reference electrode 18 has a straight portion 26, which is located between and extends along one of the two side edges of the lower surface of the electrolytic solution retainer 25 and the corresponding side edge of the cutout recess 20, at some distances from these side edges of the electrolytic solution retainer 25 and the cutout recess 20. A plurality of projecting portions (for example two projecting portions 27) project at a right angle to the straight portion 26 from the inner side edge of the straight portion 26. The inner side edge of the straight portion 26 means the side edge that faces towards the other side edge of the electrolytic solution retainer 25. The projecting portions 27 are spaced apart and extend parallel to each other. The projecting portions 27 are located closer to the inner end of the cutout recess 20 than to its open end.

The counter electrode 19, too, has a straight portion 28, which is located between and extends along the other side edge of the lower surface of the electrolytic solution retainer 25 and the corresponding side edge of the cutout recess 20, at some distances from these side edges of the electrolytic solution retainer 25 and the cutout recess 20. A plurality of projecting portions (for example two projecting portions 29) project at a right angle to the straight portion 28 from the inner side edge of the straight portion 28. The inner side edge of the straight portion 28 means the side edge that faces towards the aforementioned one side edge of the electrolytic solution retainer 25. The projecting portions 29 are spaced apart and extend parallel to each other. The projecting portions 29, too, are located closer to the inner end of the cutout recess 20 than to its open end. The projecting portions 29 of the counter electrode 19 are electrically insulated from the projecting portions 27 of the reference electrode 18. One of the projecting portions 29 of the counter electrode 19 is located between the projecting portions 27 of the reference electrode 18, while the other projecting portion 29 of the counter electrode 19 is located outside one of the projecting portions 27 of the reference electrode 18.

As described above, the reference electrode 18 and the counter electrode 19 are printed on the lower surface of the electrolytic solution retainer 25. On the top of the electrolytic solution retainer 25, the base member 22 is placed in such a state that the surface on which the detection electrode 17 is printed faces downward. As a result, the electrolytic solution retainer 25 is sandwiched between the detection electrode 17 and the other electrodes, i.e. the reference electrode 18 and the counter electrode 19, in the state where the electrodes are insulated from one another.

In the state described above, the electrolytic solution 13 in the electrolytic solution storage 2 of the case 3 is guided and fed to the electrolytic solution retainer 25, which is disposed on the vertical protrusions 15 of the case 3, by capillary action via the feeding grooves 16 of the vertical protrusions 15 of the case 3. The electrolytic solution 13 fed to the electrolytic solution retainer 25 permeates thereinto and, consequently, fed to the reference electrode 18 and the counter electrode 19. Through the electrolytic solution retainer 25, the electrolytic solution 13 is also fed to the detection electrode 17. The base member 22, on which the detection electrode 17 is printed, and the electrolytic solution retainer 25, on which the reference electrode 18 and the counter electrode 19 are printed, together form the cell 21.

A sheet member, i.e. a membrane sheet 31, is contained in the electrolytic solution storage 2 of the case 3. The membrane sheet 31 is a narrow, porous band which is hydrophobic as well as gas permeable and functions to vent gas. In other words, the membrane sheet 31 is provided to be used as an air vent. The membrane sheet 31 is disposed on the electrolytic solution retainer 25 and the base member 22, which are contained in the case 3. The membrane sheet 31 is arranged so that its middle portion is in contact with at least a part of the base member 22. The two opposing, lengthwise ends of the membrane sheet 31 reach the interior of the electrolytic solution storage 2 of the case 3 in such a manner that each lengthwise end of the membrane sheet 31 passes the corresponding side edges of the electrolytic solution retainer 25 and the base member 22. The membrane sheet 31 is contained in the electrolytic solution storage 2 of the case 3 in such a state that the lengthwise ends of the membrane sheet 31 are in contact with the base face 11 of the case 3.

The membrane sheet 31 is made of fluorine-contained resin, such as polytetrafluoroethylene (PTFE). The membrane sheet 31 is capable of releasing gas in the electrolytic solution storage 2 of the case 3 through the base member 22 and then through an opening 41 of the cap 41 to the outside, regardless of the direction in which the electrochemical gas sensor 1 is oriented. By thus equilibrating the pressure in the case 3 and the outside pressure, i.e. the atmospheric pressure, the membrane sheet 31 prevents leakage of the electrolytic solution 13 contained in the electrolytic solution storage 2 of the case 3.

The horizontally extending base ends of lead portions 32a,33a,34a of three electrode pins 32,33,34, which are spaced apart and arranged parallel to one another, pass through and are fixed to the other lengthwise end of the outer wall portion 12 of the case 3, in other words the end opposite the end towards which the vertical protrusions 15 are located. Each electrode pin 32,33,34 is formed of tantalum (Ta) in the shape of an integral slender bar bent into a seamless, S-like shape. In order to ensure sufficient resistance to corrosion from the sulfuric acid contained in the electrolytic solution 13, the tantalum used to form the electrode pins 32,33,34 should desirably have a purity of more than 99.9%.

The electrode pins 32,33,34 are formed as an integral body with the case 3 by means of molding. The base ends of the lead portions 32a,33a,34a of the electrode pins 32,33,34 extend parallel to one another in the lengthwise direction of the case 3 and project to the outside of the case 3.

The distal end portions of the lead portions 32a,33a,34a, which are the portions of the electrode pins 32,33,34 that are located inside the case 3 and project inward, are bent upward, at a right angle to the base ends of the lead portions 32a,33a,34a so that first bent portions 37 are formed between the base ends and the distal ends of the lead portions 32a,33a,34a. In other words, each lead portion 32a,33a,34a is bent at a right angle at its first bent portion 37.

The distal end portion of each lead portion 32a,33a,34a passes from the base end to the distal end of each respective boss 35 and bent so as to project towards the upper portion of the case 3. Each boss 35 has a slender, tubular shape and projects upward from the base face 11 of the case 3. The bosses 35 of the case 3 are formed in a number corresponding to the number of the lead portions 32a,33a,34a (three bosses 35 in the case of the embodiment) at locations respectively corresponding to the distal ends of the lead portions 32a,33a,34a. The outermost portions of the lead portions 32a,33a,34a project from the distal ends of the bosses 35 and serve as contact portions 32b,33b,34b, which are the distal ends of the electrode pins 32,33,34. The contact portions 32b,33b,34b are bent so as to project further inward with respect to the interior of the case 3. The lead portion 32a,33a,34a and the contact portion 32b,33b,34b of each electrode are 32,33,34 are formed as an integral, seamless body.

The contact portions 32b,33b,34b of the electrode pins 32,33,34 are bent inward with respect to the interior of the case 3, at a right angle to the distal ends of the lead portions 32a,33a,34a of the electrode pins 32,33,34 respectively, so that second bent portions 38 are formed between the lead portions 32a,33a,34a and contact portions 32b,33b,34b of the electrode pins 32,33,34. In other words, each electrode pin 32,33,34 is bent at a right angle at its second bent portion 38.

The contact portions 32b,33b,34b of the electrode pins 32,33,34 are supported by a plurality of supporting protrusions 36 formed on the base face 11 of the case 3 in such a state that the contact portions 32b,33b,34b are respectively in contact with the upper ends of the supporting protrusions 36. The supporting protrusions 36 are formed in the shape of a slender, solid cylinder integrally projecting from the base face 11 of the case 3. The supporting protrusions 36 are formed in a number corresponding to the number of the contact portions 32b,33b,34b of the electrode pins 32,33,34 (three supporting protrusions 36 in the case of the embodiment) at locations respectively corresponding to the contact portions 32b,33b,34b of the electrode pins 32,33,34. Each supporting protrusion 36 and the corresponding boss 35 are spaced apart and aligned along the lengthwise direction of the case 3 so that the supporting protrusion 36 is closer to the center of the case 3 than is the boss 35. The supporting protrusions 36 support the distal end portions of the contact portions 32b,33b,34b of the electrode pins 32,33,34 so that the distal end portions of the contact portions 32b,33b,34b extend nearly parallel to the ends of the vertical protrusions 15.

The contact portion 32b of the electrode pin 32 located towards one of the widthwise end of the case 3 is in contact with the base end portion of the straight portion 26 of the reference electrode 18, which is printed on the underside of the electrolytic solution retainer 25 contained in the case 3. The contact portion 32b of the electrode pin 32 is electrically connected to the reference electrode 18. The contact portion 33b of the electrode pin 33 located towards the other widthwise end of the case 3 is in contact with the base end portion of the straight portion 28 of the counter electrode 19, which is printed on the underside of the electrolytic solution retainer 25 contained in the case 3. The contact portion 33b of the electrode pin 33 is electrically connected to the counter electrode 19.

The contact portion 34b of the electrode pin 34 located at the middle of the width of the case 3 is inserted between the top of the electrolytic solution retainer 25 contained in the case 3 and the underside of base member 22 disposed on the electrolytic solution retainer 25. The contact portion 34b of the electrode pin 34 is in contact with the contact tab 24 of the detection electrode 17, which is printed on the underside of the base member 22. The contact portion 34b of the electrode pin 34 is electrically connected to the detection electrode 17.

A circular opening 41 is formed in the upper part of the cap 4. A net structure 43 is integrally formed inside the opening 41. The net structure 43 is comprised of a plurality of evenly situated circular vent holes. The net structure 43 is located at the middle of the width of the top of the cap 4 and closer to one of the lengthwise ends than to the other end. To be more specific, the opening 41 is formed at such a location that when the cap 4 is fitted to the case 3 the opening 41 faces the detection surface 23 of the detection electrode 17, which is printed on the base member 22 disposed in the case 3. The inner diameter of the opening 41 is nearly the same as the outer diameter of the detection surface 23 of the detection electrode 17.

Gas absorption filters 44,45 are placed from the outside into the opening 41. The gas absorption filters 44,45 are two cloth filters comprised of activated carbon in the form of felt or cloth. The type and/or quantity of the gas absorption filters 44,45 can be selected according to the gas or gases to be detected so as to improve their absorption characteristics and achieve effective removal of organic substance.

A capillary 47 is removably fitted in the opening 41. The capillary 47 serves as a lid having a cylindrical shape with a bottom. A gas intake 46 is formed at the center of the capillary 47. The diameter of each capillary 47 that can be used is determined in accordance with a gas to be detected. A water repellent filter 48 formed of polytetrafluoroethylene (PTFE) or the like is attached over the capillary 47, which is fitted in the opening 41 of the cap 4. The water repellent filter 48 is also dustproof and waterproof.

Figure 2:
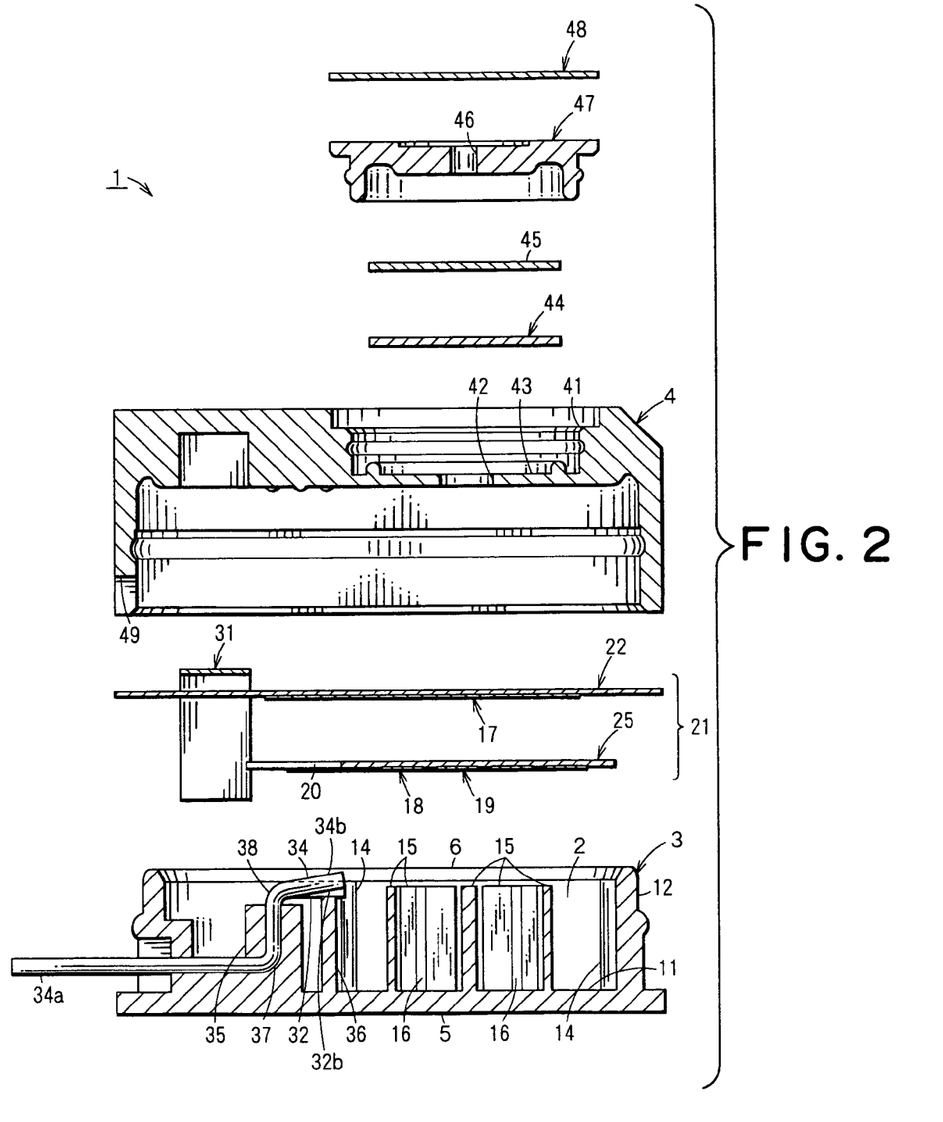
FIG. 2 is an exploded sectional view of said electrochemical sensor.
Figure 3:
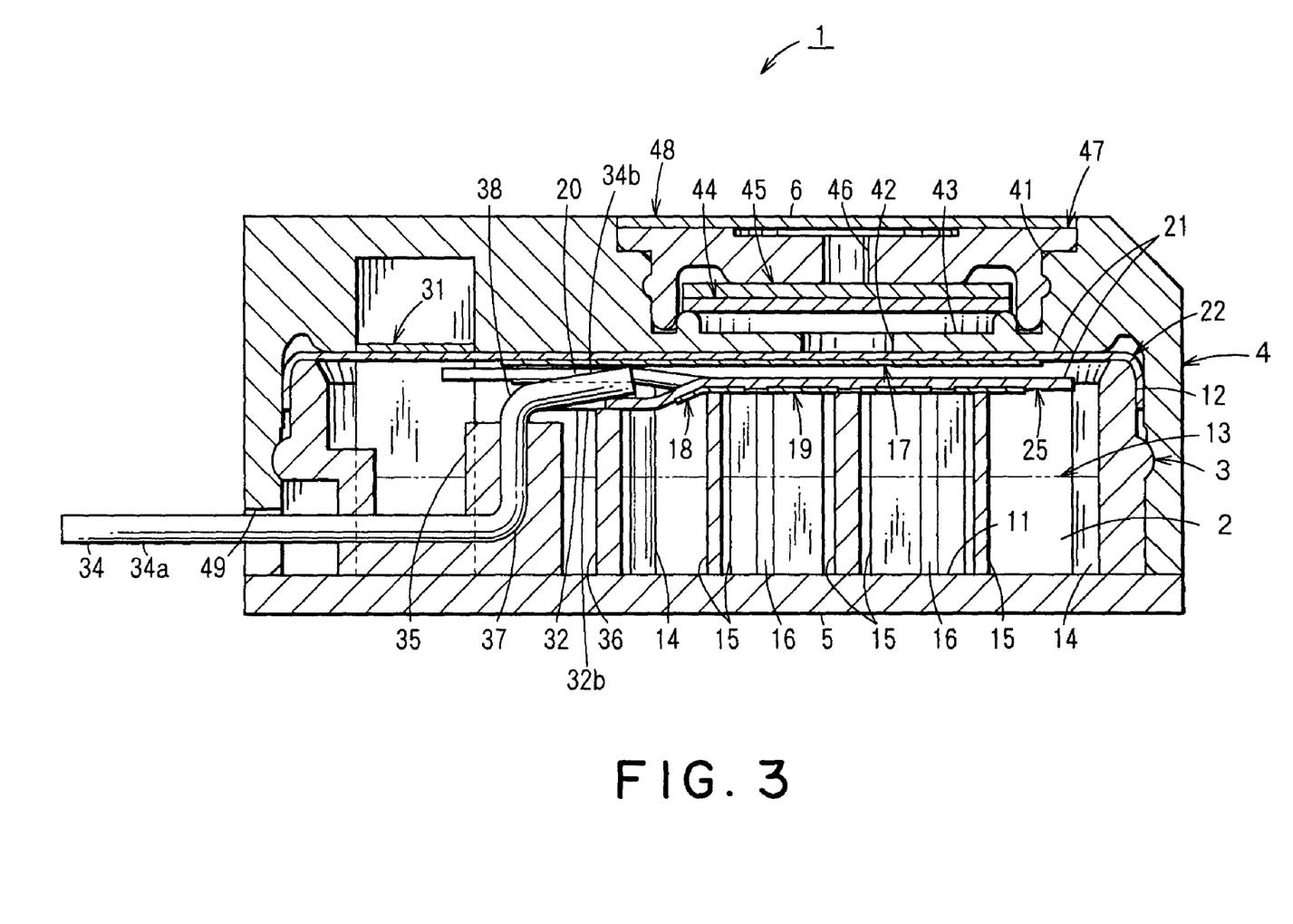
FIG. 3 is a sectional view of said electrochemical sensor.
Figure 4:
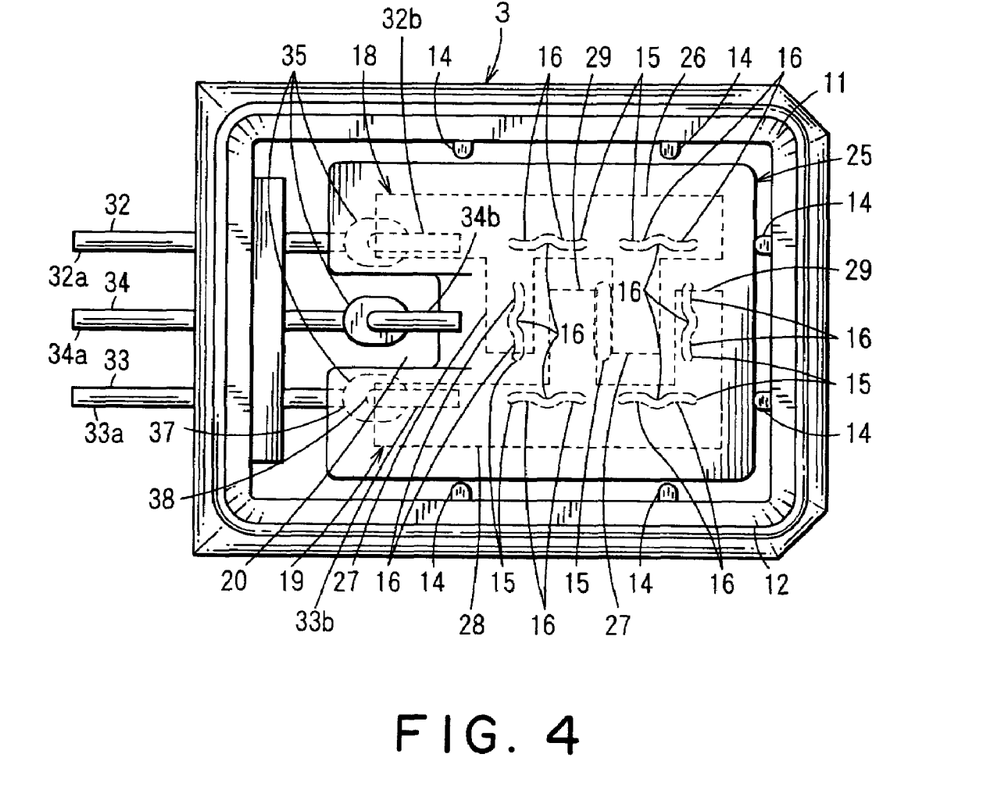
FIG. 4 is a schematic top view of said electrochemical sensor.
Figure 5:
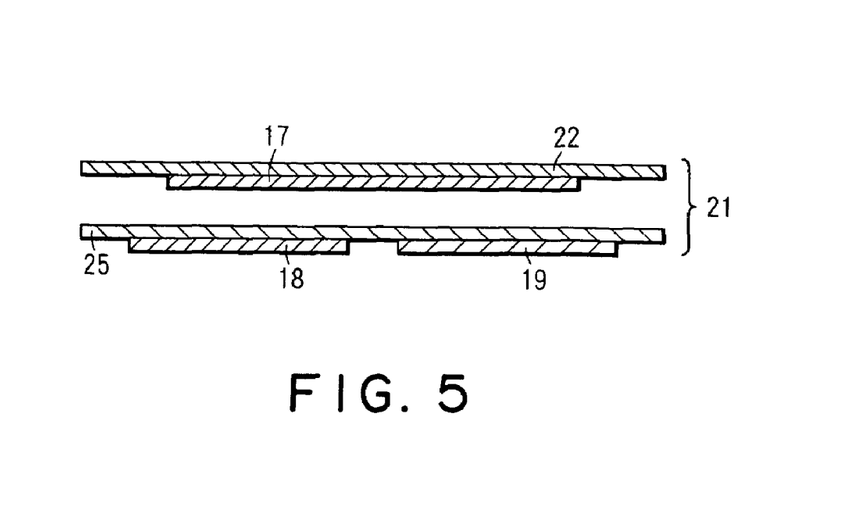
FIG. 5 is a sectional view of a cell of said electrochemical sensor.

As shown in FIGS. 2 and 3, fitting recesses 49 are formed at the edge located at the other lengthwise end of the cap 4, i.e. the end opposite the end to which the opening 41 is formed. When the cap 4 is fitted to the case 3, the fitting recesses 49 enable the snug fitting of the cap 4 to the case 3 by permitting the base portions of the lead portions 32a,33a,34a of the electrode pins 32,33,34, which project to the outside of the case 3, to fit in the respective fitting recess 49. The fitting recesses 49 are formed in a number corresponding to the number of the electrode pins 32,33,34 (three fitting recesses 49 in the case of the embodiment) at locations respectively corresponding to the base ends of the lead portions 32*a*,33*a*,34*a* of the electrode pins 32,33,34. Each fitting recess 49 is in the shape of a recessed groove that extends in the lengthwise direction of the cap 4 and has a width greater than the outer diameter of the lead portion 32*a*,33*a*,34*a* of the corresponding electrode pin 32,33,34.

Next, how to assemble the electrochemical gas sensor 1 of the embodiment described above is explained.

A given quantity of electrolytic solution 13 is injected into the electrolytic solution storage 2 of the case 3 beforehand. Of the electrode pins 32,33,34 formed as an integral body with the case 3, the contact portions 32*b*,33*b* of the electrode pins 32,33 that are located towards the two widthwise ends of the case 3 are bent inward in relation to the interior of the case 3.

Next, the electrolytic solution retainer 25 is positioned so that the surface on which the reference electrode 18 and the counter electrode 19 are printed faces downward. In this state, the electrolytic solution retainer 25 is placed on the vertical protrusions 15 of the case 3 so that the inner ribs 14 are located outside the electrolytic solution retainer 2.

During this step of positioning the electrolytic solution retainer 25, the contact portion 34 of the middle electrode pin 34, which is located at the widthwise center of the case 3, is passed through the cutout recess 20 of the electrolytic solution retainer 25. Also in this step, the base end portion of the straight portion 26 of the reference electrode 18 printed on the electrolytic solution retainer 25 is brought into contact with the contact portion 32*b* of the electrode pin 32, which is located towards one of the widthwise ends of the case 3. The base end portion of the straight portion 28 of the counter electrode 19 printed on the electrolytic solution retainer 25 is brought into contact with the distal end portion of the contact portion 33*b* of the electrode pin 33, which is located towards the other widthwise end of the case 3.

In this state, the contact portion 34*b* of the electrode pin 34 that is located at the middle of the width of the case 3 is bent inward in relation to the interior of the case 3 so that the contact portion 34*b* of the electrode pin 34 is brought into contact with the top of the electrolytic solution retainer 25.

Thereafter, the base member 22 is placed on the electrolytic solution retainer 25 in the case 3 in such a state that the surface of the base member 22 on which the detection electrode 17 is printed faces downward, with the contact tab 24 of the detection electrode 17 facing towards the electrode pins 32,33,34 in the case 3. When the base member 22 is properly placed on the electrolytic solution retainer 25, the rim of the base member 22 uniformly extends beyond the outer wall portion 12 of the case 3.

In this step of positioning the base member 22, the contact tab 24 of the detection electrode 17 printed on the base member 22 is brought into contact with the contact portion 34*b* of the electrode pin 34, which is located at the middle of the width of the case 3 and projects to the top of the electrolytic solution retainer 25 contained in the case 3.

In this state, the rim of the cap 4 is fitted around the outer wall portion 12 of the case 3 while the rim of the base end 22 is held between the outer wall portion 12 of the case 3 and the rim of the cap 4 so that the base end portions of the lead portions 32*a*,33*a*,34*a* of the electrode pins 32,33,34, which project from the outer wall portion 12 of the case 3, respectively pass through the fitting recesses 49 of the cap 4.

After appropriate gas absorption filters 44,45 are fitted in the opening 41 of the cap 4 should the necessity arise, the capillary 47 is fitted in the opening 41 of the cap 4.

Should the necessity arise, the water repellent filter 48 can be placed over the capillary 47 so as to close off the gas intake 46, which is an opening formed in the capillary 47.

As described above, the reference electrode 18 and the counter electrode 19 are formed of the same material directly on the electrolytic solution retainer 25 in the same production process by screen printing. In other words, the embodiment described above enables the production of the reference electrode 18, the counter electrode 19, and the electrolytic solution retainer 25 as a single component. Therefore, by thus reducing the number of parts of the electrochemical gas sensor 1 that includes the reference electrode 18, the counter electrode 19, and the electrolytic solution retainer 25, the present embodiment facilitates production of the electrochemical gas sensor 1 as well as reduction of its size.

The reference electrode 18 and the counter electrode 19 are printed on the same planar surface of the electrolytic solution retainer 25 and electrically insulated from each other. By thus enabling the simultaneous formation of the reference electrode 18 and the counter electrode 19 on one planar surface of the electrolytic solution retainer 25, the embodiment facilitates formation of the reference electrode 18 and the counter electrode 19 on the electrolytic solution retainer 25, and, consequently, simplifies the production process of the electrochemical gas sensor 1 that includes the reference electrode 18, the counter electrode 19 and the electrolytic solution retainer 25.

Furthermore, when the electrochemical gas sensor 1 is in the assembled state, the detection electrode 17 printed on the underside of the base member 22 is sandwiched between the base member 22 and the electrolytic solution retainer 25, and the reference electrode 18 and the counter electrode 19 printed on the underside of the electrolytic solution retainer 25 are positioned in the case 3 so as to face the electrolytic solution storage 2 of the case 3 and the electrolytic solution 13 in the electrolytic solution storage 2. Because of this configuration, the cell 21, which consists of the detection electrode 17, the reference electrode 18, the counter electrode 19, the base member 22 and the electrolytic solution retainer 25, can be formed by a reduced number of parts and be consequently made thinner and more compact.

As a plurality of vertical protrusions 15 are formed inside the electrolytic solution storage 2 of the case 3 and adapted to function as supports, the electrolytic solution retainer 25 and the base member 22 are held between the case 3 and the cap 4 by the vertical protrusions 15 without the danger of deformation of the electrolytic solution retainer 25 or the base member 22. The vertical protrusions 15 also ensure that the electrolytic solution retainer 25 is in close contact with the detection electrode 17, which is printed on the base member 22.

Providing the vertical protrusions 15 described above makes it possible to support the electrolytic solution retainer 25 and the base member 22 between the case 3 and the cap 4 without the necessity of providing another member in the electrolytic solution storage 2 of the case 3 or other means that would increase the number of parts. Therefore, this configuration enables the further reduction of the number of parts of the electrochemical gas sensor 1 and further facilitates production of the electrochemical gas sensor 1 as well as reduction of its size.

Feeding grooves 16 are formed in the sides of a number of the vertical protrusions 15 so that the electrolytic solution 13, which is in the electrolytic solution storage 2, is guided and permeated into the electrolytic solution retainer 25 by means of capillary action via the feeding grooves 16. As the electrolytic solution 13 in the electrolytic solution storage 2 can be guided and permeated into the electrolytic solution retainer 15 without the necessity of providing another member in the electrolytic solution storage 2 of the case 3 or other means that would increase the number of parts, this configuration enables the further reduction of the number of parts of the electrochemical gas sensor 1 and further facilitates production of the electrochemical gas sensor 1 as well as reduction of its size.

The vertical protrusions 15 are spaced apart on the central part of the base face 11 of the case 3 so that the electrolytic solution 13 permeates primarily into the space between the reference electrode 18 and the counter electrode 19 of the electrolytic solution retainer 25 to be placed on the vertical protrusions 15, which are provided with the feeding grooves 16. This configuration of the reference electrode 18 and the counter electrode 19 ensures the accurate sensitivity of the electrochemical gas sensor 1.

Furthermore, the electrolytic solution retainer 25 is formed of glass wool. As this feature facilitates production of the electrolytic solution retainer 25 and also makes it possible to form the reference electrode 18 and the counter electrode 19 on a surface of the electrolytic solution retainer 25 by screen printing or a similar process, this feature further facilitates production of the reference electrode 18 and the counter electrode 19 on the electrolytic solution retainer 25.

Using screen printing to print the reference electrode 18 and the counter electrode 19 on a surface of the electrolytic solution retainer 25 permits the catalyst contained in the reference electrode 18 and the counter electrode 19 to permeate deep into the electrolytic solution retainer 25 and consequently increase the degree of contact of the reference electrode 18 and the counter electrode 19 with the electrolytic solution retainer 25. As a result of this feature, a reference electrode 18 and a counter electrode 19 that are highly resistant to vibration and impact and not prone to peeling resulting from vibration or impact can be formed on the electrolytic solution retainer 25 in a simple, reliable configuration.

A membrane sheet 31 formed of a narrow, porous band which is hydrophobic as well as gas permeable is provided with its middle portion being located on and in contact with the base member 22. The membrane sheet 31 is disposed in the electrolytic solution storage 2 of the case 3 with the two opposing lengthwise ends of the membrane sheet 31 in contact with the base face 11 of the case 3 in such a manner that each lengthwise end of the membrane sheet 31 passes the corresponding side edges of the electrolytic solution retainer 25 and the base member 22. This configuration makes it possible to release gas in the electrolytic solution storage 2 of the electrochemical gas sensor 1 to the outside, without providing the case 3 or the cap 4 with any other opening or means to drain gas, regardless of the direction in which the electrochemical gas sensor 1, which is comprised of the case 3 and the cap 4, is oriented.

As the electrolytic solution 13 in the electrolytic solution storage 2 of the case 3 is aqueous solution of sulfuric acid, which is normally hygroscopic, its hygroscopicity causes the electrolytic solution 13 to absorb moisture in the atmosphere and gradually increase the quantity of the electrolytic solution 13, resulting in gradual increase of the pressure in the electrolytic solution storage 2, in which the electrolytic solution 13 is stored.

At that time, however, the gas in the electrolytic solution storage 2 is vented through the membrane sheet 31 and the base member 22 and released from the opening 41 of the cap 4 to the outside so that the pressure in the electrolytic solution storage 2 is in equilibrium with the outside pressure. Leakage of the electrolytic solution 13 in the electrolytic solution storage 2 of the case 3 can thus be prevented easily and reliably with a simple configuration.

As the electrode pins 32,33,34 are formed as an integral body with the case 3 by means of molding, the electrode pins 32,33,34 and the case 3 are formed as a single component, thereby simplifying the structure of the electrochemical gas sensor 1, which includes the electrode pins 32,33,34 and the case 3. As the number of parts is reduced, the number of processing steps required to assemble the electrochemical gas sensor 1, too, is reduced. In other words, the manufacturability of the electrochemical gas sensor 1 is improved. Furthermore, as the electrode pins 32,33,34 are electrically insulated from one another by the outer wall portion 12 of the case 3, leakage between the electrode pins 32,33,34 is prevented.

The contact portions 32$b$,33$b$,34$b$ of the electrode pins 32,33,34 are respectively in contact with the reference electrode 18, the counter electrode 19, and the detection electrode 17. The reference electrode 18, the counter electrode 19, and the detection electrode 17 are held in the case 3 by using the spring function of the second bent portions 38 of the electrode pins 32,33,34. This feature ensures not only the more reliable, immovable retention of the reference electrode 18, the counter electrode 19, and the detection electrode 17 inside the case 3 but also more reliable contact of the contact portions 32$b$,33$b$,34$b$ of the electrode pins 32,33,34 with the reference electrode 18, the counter electrode 19, and the detection electrode 17.

According to the embodiment described above, the reference electrode 18 and the counter electrode 19 are both printed on a surface of the electrolytic solution retainer 25. However, functions and effects similar to those of the embodiment described above can be achieved by printing either the reference electrode 18 or the counter electrode 19 on a surface of the electrolytic solution retainer 25 to form the electrolytic solution retainer 25 and either one of the reference electrode 18 or the counter electrode 19 into a single component.

The reference electrode 18, the counter electrode 19 and the electrolytic solution retainer 25 may be formed as a single component by printing either the reference electrode 18 or the counter electrode 19 on a surface of the electrolytic solution retainer 25 and printing the other electrode on the other surface of the electrolytic solution retainer 25. Such a configuration, too, is capable of achieving functions and effects similar to those of the embodiment described above. Another benefit of this configuration is that the reference electrode 18 and the counter electrode 19 can be formed on a smaller electrolytic solution retainer 25 than one used in the above embodiment, where the reference electrode 18 and the counter electrode 19 are formed on the same surface of the electrolytic solution retainer 25. As the electrolytic solution retainer 25 can be made even more compact, further reduction of the dimensions of the electrochemical gas sensor 1 is possible.

According to the embodiment described above, a plurality of vertical protrusions 15 are provided on the base face 11 inside the electrolytic solution storage 2 of the case 3. However, a single vertical protrusion 15 may be sufficient, provided that it is capable of supporting the electrolytic solution retainer 25 and the base member 22 between the case 3 and the cap 4 without the possibility of deformation of the electrolytic solution retainer 25 or the base member 22.

Whether the shape of the fitting grooves 16 formed in the vertical protrusions 15 is round or has sharp corners does not have a significant influence on the capillary action via the fitting grooves. 16. Therefore, the fitting grooves 16 may have any desired shape, provided that they are capable of supplying the electrolytic solution retainer 25 with the electrolytic solution 13 stored in the electrolytic solution storage 2 of the case 3 by causing the electrolytic solution 13 to permeate into the electrolytic solution retainer 25 by capillary action.

Although the electrode pins 32,33,34 to be electrically connected to the detection electrode 17, the reference electrode 18, and the counter electrode 19 are formed integrally with the case 3 by molding in the case of the embodiment, the electrode pins 32,33,34 may be formed with the cap 4 by molding or provided between the case 3 and the cap 4.

Each electrode pin 32,33,34 is formed of tantalum as an integral, seamless body in the case of the embodiment. However, the electrode pin 32,33,34 may be formed as an integral, seamless body of an alloy that contains tantalum.

According to the embodiment described above, each electrode pin 32,33,34 is formed into an S-like shape by bending the electrode at the first bent portion 37 and the second bent portion 38 so as to ensure that the electrode pin 32,33,34 has a spring function. However, it is sufficient to provide each electrode pin 32,33,34 with at least one bent portion, as long as the electrode pins 32,33,34 have a sufficient spring force to reliably hold the detection electrode 17, the reference electrode 18, and the counter electrode 19 in the case 3.

WORKING EXAMPLE

In order to determine the material for the electrode pins 32,33,34, a test was performed to evaluate the ability of each material to resist the sulfuric acid to be used in the electrolytic solution 13.

SUS303A, SUS316L, SUS321, Nickel (Ni), Monel (product name of Daido-Special Metals Ltd.) (alloy of Ni—Co—Cu), Hastelloy C-276 (product name of Haynes Stellite Co.) (alloy of Ni—Mo—Cr), titanium (Ti), tantalum (Ta), gold plate (base metal: phosphor bronze), gold (Au), palladium (Pd), and platinum (Pt) were chosen as metals to be tested as possible metals for the electrode pins 32,33,34.

The samples consisting of the metals described above were separately and individually immersed in 40% sulfuric acid solution at 50° C. to observe changes in the test metals. Results of the test are shown in Table 1.

TABLE 1

Sulfuric Acid Resistance Test — Test Conditions: immerse in 40% sulfuric acid solution at 50° C.

| Test metals | 2 days | 7 days | 30 days | 60 days | Conclusion |
|---|---|---|---|---|---|
| SUS303A | Δ | X | X | X | unusable |
| SUS316L | Δ | X | X | X | unusable |
| SUS321 | X | X | X | X | unusable |
| Nickel(Ni) | X | X | X | X | unusable |
| Nickel(Ni-Co-Cu) | Δ | X | X | X | unusable |
| Hastelloy C-276 (Ni-Mo-Cr) | Δ | X | X | X | unusable |
| Titanium(Ti) | ○ | Δ | X | X | unusable |
| Tantalum(Ta) | ○ | ○ | ○ | ○ | usable |
| Gold plate (base metal: phosphor bronze) | Δ | X | X | X | unusable |
| Gold(Au) | ○ | ○ | ○ | ○ | usable |
| Palladium(Pd) | ○ | Δ | X | X | unusable |
| Platinum(Pt) | ○ | ○ | ○ | ○ | usable |

X: conspicuous melting or other changes;
Δ: same change;
○: no change

It was concluded from the results shown in Table 1 that using tantalum, gold, or platinum as the material for the electrode pins 32,33,34 is most appropriate.

Next, another test was performed on each sample material that is resistant to sulfuric acid and had been selected by the first working example described above. This test was performed to examine the Young's modulus and the Vickers hardness of each sample and evaluate the ability to contact of each sample in order to evaluate the degree of suitability of the mechanical characteristics of these metals for the electrode pins 32,33,34.

Tantalum, gold, and platinum, all of which had produced satisfactory results in the first working example, were chosen as the subject metals of the test. Results of the test are shown in Table 2.

TABLE 2

| Subject metal | Elasticity Young's modulus | Hardness Vickers hardness | Conclusion |
|---|---|---|---|
| Tantalum (Ta) | $18.6 \times 10^{10}$ | 60–100 | satisfactory |
| Gold (Au) | $7.8 \times 10^{10}$ | 20 | unsatisfactory |
| Platinum (Pt) | $16.8 \times 10^{10}$ | 38–40 | unsatisfactory |

As is evident from the results shown in Table 2, electrode pins 32,33,34 formed of tantalum have a high Young's modulus and a high level of Vickers hardness number. Therefore, the electrode pins 32,33,34 can be kept in contact with the detection electrode 17, the reference electrode 18, and the counter electrode 19 in a satisfactory state and are not prone to cause any problems even if they are subject to repetition of plug-in/out into and from sockets (not shown) or the like.

Electrode pins 32,33,34 formed of gold are soft and prone to deformation due to a low Young's modulus and a low level of Vickers hardness number. Therefore, electrode pins 32,33,34 formed of gold are prone to contact failure with the detection electrode 17, the reference electrode 18, and the counter electrode 19, which failure would result in significant change in performance characteristics of the electrochemical gas sensor 1, and easy to be damaged or deformed when inserted into sockets or the like.

Electrode pins 32,33,34 formed of platinum have a similar level of Young's modulus to those formed of tantalum and therefore has the ability to resist a deforming force. However, as they have a low Vickers hardness (in other words they are soft), they are prone to damage or deformation when inserted into sockets or the like.

Therefore, in cases where the electrolytic solution 13 contained in the electrolytic solution storage 2 of the case 3 is aqueous solution of sulfuric acid, each electrode pin 32,33,34 formed integrally with the case 3 by molding is formed of tantalum as an integral, seamless body. This provides a simplified structure and eliminates the necessity of welding or other connecting work. As tantalum is resistant to corrosion from sulfuric acid and relatively inexpensive, using tantalum as above ensures that the electrode pins 32,33,34 have sufficient resistance to corrosion from sulfuric acid and consequently improves manufacturability of the electrochemical gas sensor 1.

As tantalum has relatively high degree of rigidity, using tantalum as the material to form each electrode pin 32,33,34 as an integral, seamless body ensures that each one of the electrodes, i.e. the detection electrode 17, the reference electrode 18, or the counter electrode 19, is securely supported either in the case 3 or the cap 4 because of the rigidity of the corresponding electrode pin 32,33,34, which has at least one bent portion, such as the bent portion 38.

The invention claimed is:

1. An electrochemical sensor including:
a base member which has a porous, sheet-like shape and is hydrophobic as well as gas permeable;
a detection electrode which is included in the base member and contains a catalyst and hydrophobic resin;
a reference electrode and a counter electrode, each of which contains a catalyst and hydrophobic resin; and
an electrolytic solution retainer which has a sheet-like shape and is hydrophilic as well as electrically insulating, said electrolytic solution retainer being provided with either one of or both the reference electrode and the counter electrode,
wherein the reference electrode is formed on one of the planar surfaces of the electrolytic solution retainer, and the counter electrode is formed on the other planar surface of the electrolytic solution retainer.

2. An electrochemical sensor as claimed in claim 1, wherein:
the reference electrode and the counter electrode are formed on one of the planar surfaces of the electrolytic solution retainer.

3. An electrochemical sensor as claimed in claim 1, wherein:
the reference electrode and the counter electrode are formed of the same material on the electrolytic solution retainer.

4. An electrochemical sensor as claimed in claim 1, wherein the electrolytic solution retainer is formed of glass wool.

5. An electrochemical sensor including:
a case having an electrolytic solution storage;
a cap adapted to be fitted to the case;
a cell adapted to be contained in the case by means of said cap and including:
a base member which has a porous, sheet-like shape and is hydrophobic as well as gas permeable,
a detection electrode which is included in the base member and contains a catalyst and hydrophobic resin,
a reference electrode and a counter electrode, each of which contains a catalyst and hydrophobic resin; and
an electrolytic solution retainer which has a sheet-like shape and is hydrophilic as well as electrically insulating, said electrolytic solution retainer being provided with either one of or both the reference electrode and the counter electrode; and
electrode pins which are included in either one of or both the case and the cap and adapted to be connected to said cell,
wherein the electrochemical sensor further includes at least one post element that is located inside the electrolytic solution storage of the case and provided with one or more grooves adapted to guide the electrolytic solution contained in the electrolytic solution storage to the electrolytic solution retainer of the cell.

6. An electrochemical sensor as claimed in claim 5, wherein:
the electrochemical sensor further includes a plurality of post elements adapted to support the cell, which is contained in the electrolytic solution storage of the case, and
one or more of said post elements are provided with grooves adapted to guide the electrolytic solution contained in the electrolytic solution storage to the electrolytic solution retainer of the cell.

7. An electrochemical sensor as claimed in claim 5, wherein:
the electrolytic solution retainer is formed of glass wool.

8. An electrochemical sensor as claimed in claim 5, wherein:
the electrochemical sensor further includes a porous sheet which is hydrophobic as well as gas permeable and contained in said case in such a state as to be in contact with the electrolytic solution storage of the case and the base member positioned in the case.

9. An electrochemical sensor including:
a case having an electrolytic solution storage adapted to store therein electrolytic solution that contains sulfuric acid;
a cap adapted to be fitted to the case;
electrodes consisting of a detection electrode, a reference electrode, and a counter electrode, each of which is adapted to be contained in either the case or the cap; and
electrode pins formed of tantalum or an alloy containing tantalum, each electrode pin having:
a contact portion adapted to secure each respective one of said electrodes, i.e. the detection electrode, the reference electrode, or the counter electrode, in the case or the cap in such a state as to be in contact with the electrode, and
a lead portion that is drawn out of either the case or the cap,
wherein the contact portion and the lead portion of each electrode pin is formed as a seamless, integral body.

10. An electrochemical sensor as claimed in claim 9, wherein:
the electrode pins are formed integrally with either one of the case or the cap.

11. An electrochemical sensor as claimed in claim 9, wherein:
each electrode pin has at least one bent portion to immovably hold each respective one of the detection electrode, the reference electrode, or the counter electrode in either the case or the cap.

12. An electrochemical sensor as claimed in claim 9, wherein:
the electrode pins are formed integrally with the case by molding.

13. An electrochemical sensor including:

a case having an electrolytic solution storage;

a cap adapted to be fitted to the case;

a cell adapted to be contained in the case by means of said cap and including:
- a base member which has a porous, sheet-like shape and is hydrophobic as well as gas permeable,
- a detection electrode which is included in the base member and contains a catalyst and hydrophobic resin,
- a reference electrode and a counter electrode, each of which contains a catalyst and hydrophobic resin; and
- an electrolytic solution retainer which has a sheet-like shape and is hydrophilic as well as electrically insulating, said electrolytic solution retainer being provided with either one of or both the reference electrode and the counter electrode; and electrode pins which are included in either one of or both the case and the cap and adapted to be connected to said cell, wherein the electrochemical sensor further includes a plurality of post elements adapted to support the cell, which is contained in the electrolytic solution storage of the case, and one or more of said post elements are provided with grooves adapted to guide the electrolytic solution contained in the electrolytic solution storage to the electrolytic solution retainer of the cell.

14. An electrochemical sensor as claimed in claim 13, wherein the electrolytic solution retainer is formed of glass wool.

15. An electrochemical sensor as claimed in claim 13, wherein the electrochemical sensor further includes a porous sheet which is hydrophobic as well as gas permeable and contained in said case in such a state as to be in contact with the electrolytic solution storage of the case and the base member positioned in the case.

\* \* \* \* \*